United States Patent [19]
Beasley, Jr.

[11] Patent Number: 5,776,928
[45] Date of Patent: Jul. 7, 1998

[54] METHOD FOR TREATING DYSKINESIAS WITH OLANZAPINE

[75] Inventor: Charles M. Beasley, Jr., Indianapolis, Ind.

[73] Assignee: Eli Lilly and Company, Indianapolis, Ind.

[21] Appl. No.: 422,177

[22] Filed: Apr. 21, 1995

[51] Int. Cl.$^6$ .................................................. A61K 31/55
[52] U.S. Cl. ............................................................. 514/220
[58] Field of Search ......................................... 514/220

[56] References Cited

U.S. PATENT DOCUMENTS 5,229,382  7/1993  Chakrabarti et al. .................. 514/220

OTHER PUBLICATIONS

Moore et al., *Chemical Abstracts*, vol. 117, No. 19, abstract No. 184704w, 1992, p. 70.

Gerlach, et al., "Intolerance to neuroleptic drugs: the art of avoiding extrapyramidal syndromes", *European Psychiatry*, 10:1 (1994).

Moore, et al., "The behavioral pharmacology of olanzapine, a novel Atypical Antipsychotic Agent", *J. Pharm. Exp. Ther.*, 262:2 pp. 545–551 (1992).

Tamminga, et al., "Clozapine in tardive dyskinesia: observations from human and animal model studies" *J. Clin. Psychiatry*, 55:9, pp. 102–106 (1994).

*Primary Examiner*—William R. A. Jarvis
*Attorney, Agent, or Firm*—MaCharri Vorndran-Jones; David E. Boone

[57] ABSTRACT

The invention provides a method for treating a dyskinesias comprising administering an effective amount of 2-methyl-4-(4-methyl-1-piperazinyl)-10H-thieno[2,3-b][1,5] benzodiazepine.

11 Claims, No Drawings

METHOD FOR TREATING DYSKINESIAS WITH OLANZAPINE

FIELD OF THE INVENTION

This invention provides a method for using 2-methyl-4-(4-methyl-1-piperazinyl)-10H-thieno[2,3-b][1,5] benzodiazepine, which is also known as alanzapine for the treatment of dyskinesias.

BACKGROUND OF THE INVENTION

Voluntary movement is the end product of a complex sequence of neural and neuromuscular events. When one or more motor system components are damaged or diseased, abnormal movement patterns emerge. Such movement disorders may or may not cause weakness or reflex changes; however, the hallmark characteristic is involuntary movement or paucity of movement. Such movement disorders may result in hyperkinesia or hypokinesia, and with movements of varying frequency, intensity, and amplitude. The causes of such movement disorders include heredity, metabolic derangements, and neurodegenerative diseases. Often such movement disorders can be caused by the use of antipsychotic agents.

Ever since antipsychotics were introduced it has been observed that patients are liable to suffer from drug-induced extrapyramidal symptoms which include drug-induced parkinsonism, acute dystonic reactions, akathisia, tardive dyskinesia and tardive dystonia. The severity of such adverse events, in a considerable number of patients, frequently results in poor compliance or termination of treatment.

For example, tardive dyskinesia often appears after several months or years of neuroleptic therapy and persists after discontinuation of the drug or drugs. Symptoms may persist indefinitely, though in some cases slow remission is observed over months or years. In general, the likelihood of remission is lower with longer exposure to neuroleptics and with increasing age of the patient. McDowell et al., *Clinical Biology*, Chapter 38, 1988.

It is known that the compound 2-methyl-4-(4-methyl-1-piperazinyl)-10H-thieno[2,3-b][1,5] benzodiazepine can provide antipsychotic activity and is less likely to induce extrapyramidal symptoms. However, Applicant has discovered that surprisingly 2-methyl-4-(4-methyl-1-piperazinyl)-10H-thieno[2,3-b][1,5] benzodiazepine can be useful for treating both natural and drug-induced dyskinesias. The compound 2-methyl-4-(4-methyl-1-piperazinyl)-10H-thieno[2,3-b][1,5] benzodiazepine is known and described in U.S. Pat. No. 5,229,382, herein incorporated by reference in its entirety.

SUMMARY OF THE INVENTION

The presently claimed invention provides a method for treating a dyskinesia comprising administering an effective amount of 2-methyl-4-(4-methyl-1-piperazinyl)-10H-thieno [2,3-b][1,5] benzodiazepine or a pharmaceutically acceptable salt thereof to a patient in need of such treatment.

DETAILED DESCRIPTION OF THE INVENTION

The 2-methyl-4-(4-methyl-1-piperazinyl)-10H-thieno[2,3-b][1,5]benzodiazepine compound is of the formula

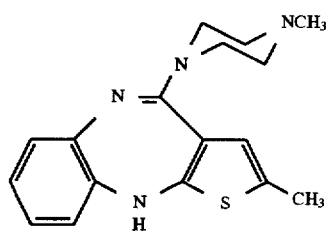

or an acid addition salt thereof. The free base of formula (I) is 2-methyl-4-(4-methyl-1-piperazinyl)-10H-thieno[2,3-b][1,5]benzodiazepine.

The substantially pure crystalline anhydrous Form I 2-methyl-4-(4-methyl-1-piperazinyl)-10H-thieno[2,3-b][1,5] benzodiazepine (Form I) has a typical X-ray powder diffraction pattern substantially as follows, using a Sieman's D5000 diffractometer equipped with a copper radiation source, wherein d represents the interplanar spacing:

| d | $I/I_1$ |
|---|---|
| 10.2689 | 100.00 |
| 8.577 | 7.96 |
| 7.4721 | 1.41 |
| 7.125 | 6.50 |
| 6.1459 | 3.12 |
| 6.071 | 5.12 |
| 5.4849 | 0.52 |
| 5.2181 | 6.86 |
| 5.1251 | 2.47 |
| 4.9874 | 7.41 |
| 4.7665 | 4.03 |
| 4.7158 | 6.80 |
| 4.4787 | 14.72 |
| 4.3307 | 1.48 |
| 4.2294 | 23.19 |
| 4.141 | 11.28 |
| 3.9873 | 9.01 |
| 3.7206 | 14.04 |
| 3.5645 | 2.27 |
| 3.5366 | 4.85 |
| 3.3828 | 3.47 |
| 3.2516 | 1.25 |
| 3.134 | 0.81 |
| 3.0848 | 0.45 |
| 3.0638 | 1.34 |
| 3.0111 | 3.51 |
| 2.8739 | 0.79 |
| 2.8102 | 1.47 |
| 2.7217 | 0.20 |
| 2.6432 | 1.26 |
| 2.6007 | 0.77 |

Form II 2-methyl-4-(4-methyl-1-piperazinyl)-10H-thieno [2,3-b][1,5] benzodiazepine (Form II) has a typical X-ray powder diffraction pattern substantially as follows, using a Sieman's D5000 diffractometer equipped with a copper radiation source, wherein d represents the interplanar spacing:

| d | $I/I_1$ |
|---|---|
| 9.9463 | 100.00 |
| 8.5579 | 15.18 |
| 8.2445 | 1.96 |
| 6.8862 | 14.73 |
| 6.3787 | 4.25 |
| 6.2439 | 5.21 |
| 5.5895 | 1.10 |
| 5.3055 | 0.95 |
| 4.9815 | 6.14 |

-continued

| d | I/I$_1$ |
|---|---|
| 4.8333 | 68.37 |
| 4.7255 | 21.88 |
| 4.6286 | 3.82 |
| 4.533 | 17.83 |
| 4.4624 | 5.02 |
| 4.2915 | 9.19 |
| 4.2346 | 18.88 |
| 4.0855 | 17.29 |
| 3.8254 | 6.49 |
| 3.7489 | 10.64 |
| 3.6983 | 14.65 |
| 3.5817 | 3.04 |
| 3.5064 | 9.23 |
| 3.3392 | 4.67 |
| 3.2806 | 1.96 |
| 3.2138 | 2.52 |
| 3.1118 | 4.81 |
| 3.0507 | 1.96 |
| 2.948 | 2.40 |
| 2.8172 | 2.89 |
| 2.7589 | 2.27 |
| 2.6597 | 1.86 |
| 2.6336 | 1.10 |
| 2.5956 | 1.73 |

The x-ray powder diffraction patterns set forth herein were obtained with a copper K of wavelength=1.541A. The interplanar spacings in the column marked "d" are in Angstroms. The typical relative intensities are in the column marked "I/I$_1$". The detector was a Kevex silicon lithium solid state detector.

As used herein "substantially pure" shall refer to anhydrous Form I associated with <5% Form II; and most preferably it shall refer to <2% Form II. It is further preferred that "substantially pure" shall refer to <0.5% non-Form I polymorph.

As used herein "substantially pure" shall refer to anhydrous Form I associated with about <5% Form II; and most preferably it shall refer to about <2% Form II. It is further preferred that "substantially pure" shall refer to <0.5% related substances. When the Form I polymorph is formulated as a pharmaceutical composition, "substantially pure" shall preferably refer to about <15% Form II polymorph; more preferably, the term shall refer to about <10% Form II polymorph when the Form I polymorph is formulated as a pharmaceutical, and it is especially preferred that the term shall refer to about <5% Form II polymorph when the substantially pure substance is formulated.

Typically, the technical grade 2-methyl-4-(4-methyl-1-piperazinyl)-10H-thieno[2,3-b][1,5] benzodiazepine contains less than about 5% undesired related substances and may be a mixed polymorph. Such technical grade 2-methyl-4-(4-methyl-1-piperazinyl)-10H-thieno[2,3-b][1,5] benzodiazepine may contain less than about 1% undesired related substances.

The term "crude" refers to a form of 2-methyl-4-(4-methyl-1-piperazinyl)-10H-thieno[2,3-b][1,5] benzodiazepine typically associated with undesired polymorph and/or greater than about 5% undesired related substances. Such crude grade 2-methyl-4-(4-methyl-1-piperazinyl)-10H-thieno[2,3-b][1,5] benzodiazepine may contain less than about 1% undesired related substances.

As used herein, the term "mammal" shall refer to the Mammalia class of higher vertebrates. The term "mammal" includes, but is not limited to, a human. The term "treating" as used herein includes prophylaxis of the named condition or amelioration or elimination of the condition once it has been established.

As used herein, the term "dyskinesia" or "dyskinesias" shall include neurological syndromes, natural and drug-induced, consisting of spontaneous and largely uncontrollable movements or paucity of movement. The term shall include both hyperkinesias and hypokinesias. Examples include, but are not limited to, parkinsonism, chorea, athetosis, choreathetosis, tremor, acute dystonic reactions, akathisia, neuroleptic malignant syndrome, tardive dyskinesia and tardive dystonia. It is particularly preferred that the term refers to hyperkinesias. It may be preferred that the term refers to hypokinesias. It is especially preferred that the term shall refer to tardive dyskinesia. It is further preferred that such term shall especially refer to tardive dyskinesia or tardive dystonia. It is preferred that dyskinesia shall include, but is not limited to, parkinsonism, dystonia, tardive dyskinesia, and akathisia.

The results of pharmacological studies show that 2-methyl-4-(4-methyl-1-piperazinyl)-10H-thieno[2,3-b][1,5]benzodiazepine has muscarinic cholinergic receptor activity. The compound is active at the dopamine D-1 and D-2 receptors as indicated by an IC50 of less than 1 uM in the 3H-SCH233390 (Billard, et al. Life Sciences 35:1885 (1984)) and the 3H spiperone (Seeman et al Nature 216:717 (1976)) binding assays respectively. Further, the anhydrous Form I compound is active at the 5-HT-2 receptor and 5-HT1C receptor. The complex pharmacological profile of the compound provides a medicament which can be useful for the treatment of a dyskinesia.

In vivo animal and clinical observations support that 2-methyl-4-(4-methyl-1-piperazinyl)-10H-thieno[2,3-b][1,5]benzodiazepine has a complex muscarinic receptor subtype profile. For example, rats exposed to an overdose of the compound surprisingly exhibited significant salivation. Further, clinical subjects experienced pupilary constriction rather than the expected pupilary dilation.

Tardive dyskinesia is believed to be caused by post synaptic dopamine receptor hyperactivity in the nigrostriatum. This hypersensitivity can be induced by chronic treatment with neuroleptic drugs. As with other nigrostriatum movement disorders, the balance between acetyl cholinergic and dopaminergic neural systems appears to be disturbed in tardive dyskinesia.

The usefulness of the compound for treating various dyskinesias can be supported by the following studies as described.

I. Effect on Tardive Dyskinesia using rats.

The compound is studied for its ability to reduce oral dyskinesia in fluphenazine treated rats. Fluphenazine is a widely used model for human neuroleptic induced Tardive Dyskinesia. (Waddington et al. Science 220: 530–532 (1983). Six adult male rats are maintained for fifteen weeks on ad lib food and water with fluphenazine added. The fluphenazine concentration in the water is 30 mg/l for eight weeks and 15 mg/l for the subsequent seven weeks. A control group of rats are maintained under the same conditions; however, the fluphemazine is not added to the water.

Each animal is tested for superfluous oral movement by placing it in a small transparent cage and counting the number of non-directed oral movements for five minute periods at fifteen minute intervals. After three baseline measurement periods each animal is injected with 2-methyl-4-(4-methyl-1-piperazinyl)-10H-thieno[2,3-b][1,5] benzodiazepine in vehicle or vehicle.

The animals are monitored for oral dyskinesia beginning ten minutes after the injection.

II. Inhibition of Thalamonal-induced rigor in rats.

Rigor is induced in male and female rats (Sprague Dawley strain) by the administration of 7.5 mg/kg of Thalamonal (2.5 mg/ml droperidol and 0.5 mg/ml fentanyl). After 15 minutes each test animal is immobilized in a hammock and bipolar electrode inserted into the calf muscle of one limb. The electromyogram is recorded. Thirty minutes after administration of the Thalamonal, the 2-methyl-4-(4-methyl-1-piperazinyl)-10H-thieno[2,3-b][1,5] benzodiazepine compound is administered by i.v. injection into the tail vein in increasing doses at 10 minute intervals. Six rats are used per compound and the dose necessary to reduce the intensity of the rigor by 10% and the dose required to completely abolish the rigor are determined by comparison of the integrated electromyograms obtained before and after the administration of the 2-methyl-4-(4-methyl-1-piperazinyl)-10H-thieno[2,3-b][1,5] benzodiazepine. A placebo control group, wherein the rats are injected with vehicle at 10 minute intervals, is included in the study.

III. Clinical observations.

A double-blind multicenter clinical trial was designed to assess the safety and efficacy of 2-methyl-4-(4-methyl-1-piperazinyl)-10H-thieno[2,3-b][1,5] benzodiazepine in patients wherein one aspect of the study was the effect of 2-methyl-4-(4-methyl-1-piperazinyl)-10H-thieno[2,3-b][1,5] benzodiazepine on patients with and without dyskinesia at study entry. Patients were randomized to 2-methyl-4-(4-methyl-1-piperazinyl)-10H-thieno[2,3-b][1,5] benzodiazepine or placebo. The results of the study suggest that 2-methyl-4-(4-methyl-1-piperazinyl)-10H-thieno[2,3-b][1,5] benzodiazepine can be useful for the treatment of dyskinesias.

IV. Clinical Study using schizophrenic patients.

A group of schizophrenic patients with diagnosis of tardive dyskinesia of moderate or severe degree are randomized in a double blind clinical trial. Subjects are given a full psychiatric and medical assessment prior to randomization. Each participant is treated with a clinically optimal dose of haloperidol for an initial one to six month stabilization period. Each patient is withdrawn from neuroleptic treatment for four weeks to provide neuroleptic-free assessment of their dyskinetic symptoms. At the conclusion of the first four neuroleptic free (or fixed low-dose) weeks, assessments of the dyskinetic movements are carried out using the Maryland Psychiatric Research Center (MPRC) Involuntary Motor Scale and a videotape of a semistructured motor examination (for later rating independent of clinical information by a single rater). Subjects are then blindly randomized to two different drug groups, 2-methyl-4-(4-methyl-1-piperazinyl)-10H-thieno[2,3-b][1,5]benzodiazepine plus placebo or haloperidol plus benztropine, and stratified by age and severity of dyskinesia.

The dose of neuroleptic drug is ordered by the blind study physician based on clinical psychopathologic symptom response. Patients are treated to optimal clinical response as judged by the blind study physician. Staff, patients, and all raters are blind to the drug group; one nonrating physician and one nurse are nonblind to dispense medication and monitor safety. All subjects are seen weekly for evaluation and medication review.

A full outcome assessment is done monthly, which includes ratings with MPRC Involuntary Motor Scale and a videotaped evaluation session. After 12-treatment months on the blinded medication, each volunteer begins a final four week drug-free assessment period. After the blinded portion of the protocol, each patient is treated with 2-methyl-4-(4-methyl-1-piperazinyl)-10H-thieno[2,3-b][1,5] benzodiazepine at an optimal clinical dose for an additional twelve months during which time the same ratings and rating schedule are continued.

The compound 2-methyl-4-(4-methyl-1-piperazinyl)-10H-thieno[2,3-b][1,5]benzodiazepine can be used for the methods of this invention, both in its free base and acid addition salt forms. The acid addition salts are preferably the pharmaceutically acceptable, non-toxic addition salts with suitable acids, such as those of inorganic acids, for example hydrochloric, hydrobromic, nitric, sulfuric or phosphoric acids, or of organic acids, such as organic carboxylic acids, for example glycollic, maleic, hydroxymaleic, fumaric, malic, tartaric, citric or lactic acid, or organic sulfonic acids for example methane sulfonic, ethane sulfonic, 2-hydroxyethane sulfonic, toluene-p-sulfonic or naphthalene-2-sulfonic acid.

The compound 2-methyl-4-(4-methyl-1-piperazinyl)-10H-thieno[2,3-b][1,5]benzodiazepine can be prepared using a process which comprises (a) reacting N-methylpiperazine with a compound of the formula

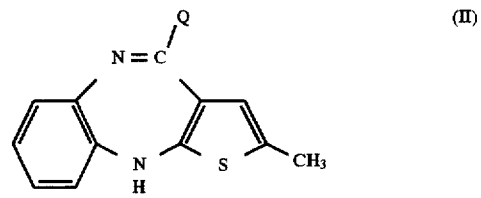

in which Q is a radical capable of being split off, or (b) ring-closing a compound of the formula

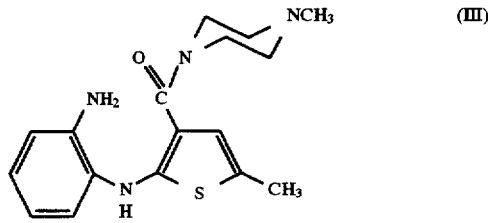

Appropriate reaction conditions and suitable values of Q can readily be chosen for these processes.

In reaction (a)the radical Q can, for example, be an amino group or a mono- or dialkyl-substituted amino group (each alkyl substituent suitably containing 1 to 4 carbon atoms), hydroxyl, thiol, or an alkoxy, alkylthio or alkylsulfonyl group suitably containing 1 to 4 carbon atoms, for example a methoxy or methylthio group, or a halogen atom, especially a chlorine atom. Preferably, Q is amino (—NH$_2$), hydroxyl or thiol, and amino is most preferred. The reaction is preferably carried out at a temperature of from 50° C. to 200° C.

When Q is amino, the intermediate of formula (II) may also exist in the imino form:

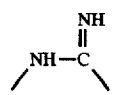

and when Q is hydroxyl or thiol, the intermediates of formula (II) may exist in their amide and thioamide forms:

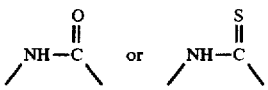

The amidine of formula (II) (Q is —NH₂), can be in salt form, for example a salt of a mineral acid such as the hydrochloride, and can be reacted with N-methylpiperazine in an organic solvent such as anisole, toluene, dimethylformamide or dimethylsulfoxide, preferably at a temperature range of 100° to 150° C.

The amidine is prepared by condensing a thiophene compound of formula

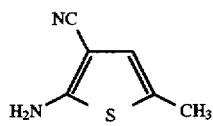

with an ortho-halonitrobenzene, in the presence of a base, for example sodium hydride, in a solvent such as tetrahydrofuran or n-butyl lithium in tetrahydrofuran, or potassium carbonate or lithium hydroxide in dimethylsulfoxide or aqueous sodium hydroxide in dimethylsulfoxide, or with a tetraalkyl-ammonium salt in a two-phase system, to form a nitronitrile of formula:

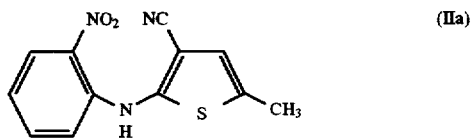

which can be simultaneously reduced and ring-closed to the amidine of formula (II) employing, for example, stannous chloride and hydrogen chloride in aqueous ethanol or, alternatively by reduction with hydrogen and palladium/ carbon or ammonium polysulfide followed by acid-catalyzed ring closure. The intermediate of formula (IIa) may be isolated using ammonium chloride (NH₄Cl) or ammonium acetate (NH₄OAc).

When Q is hydroxyl, reaction (a) is preferably carried out in the presence of titanium tetrachloride which has the ability to react with the N-methylpiperazine to form a metal amine complex. Other metal chlorides such as those of zirconium, hafnium or vanadium may also be employed. The reaction can be carried out in the presence of an acid binding agent such as a tertiary amine, for example, triethylamine.

Alternatively, the reaction can be carried out using excess of N-methylpiperazine to act as an acid-binding agent. A suitable organic solvent such as toluene or chlorobenzene can be used as a reaction medium, although the use of anisole is particularly desirable, at least as a co-solvent, in view of its ability to form a soluble complex with TiCl₄.

If desired, elevated temperatures, for example up to 200° C., can be used to hasten the reaction and a preferred temperature range for carrying out the reaction is from 80° C. to 120° C.

The intermediate amide of formula (II) (Q is —OH) can be prepared from the corresponding amidine (Q is —NH₂) by alkaline hydrolysis, or can be derived from compounds of formula

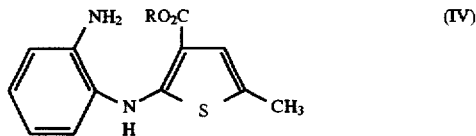

in which R is an ester group, preferably $C_{1-4}$ alkyl, by ring closure employing, for example, sodium methylsulfinyl methanide in a suitable solvent such as dimethylsulfoxide. Alternatively, the amide can be prepared by ring closure of an amino-acid, employing for example dicyclohexylcarbodiimide (DCC) in a suitable solvent such as tetrahydrofuran. The amino-acid can be obtained for example from the above esters by basic hydrolysis using for example sodium hydroxide in ethanol.

Thioamides of formula (II) (Q is —SH), iminothioethers, iminoethers or iminohalides, or other derivatives containing active Q radicals as specified above, tend to be more reactive towards N-methylpiperazine and can usually be reacted without the necessity for the presence of TiCl₄, but otherwise employing the same conditions of temperature and solvent.

The thioamide of formula (II) (Q is —SH) can be prepared by treating a solution of the corresponding amide in an anhydrous basic solvent, such as pyridine, with phosphorous pentasulfide. Similarly, the amide can be converted to the iminothioether, iminoether or iminohalide, or other derivatives containing active Q radicals, by treatment with conventional reagents such as for example in the case of the iminochloride, phosphorous pentachloride.

The intermediate compounds of formula (II) in which Q is a radical capable of being split off, particularly those in which Q is —NH₂, —OH or —SH and when Q is —NH₂ salts thereof, are novel compounds, and form a further aspect of the present invention.

With regard to reaction (b) above, the compound of formula (III) may be ring-closed by employing, for example, titanium tetrachloride as catalyst and anisole as solvent, and the reaction is preferably carried out at a temperature of 100° C. to 250° C., for example from 150° C. to 200° C.

The intermediate compound of formula (III) is preferably prepared in situ without isolation by reacting a compound of formula

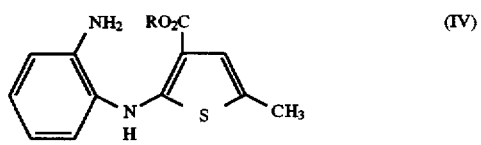

in which R is an ester group, preferably $C_{1-4}$ alkyl, with N-methylpiperazine, by heating to a temperature of between 30° C. and 120° C., for example about 100° C., in a suitable solvent such as for example anisole, and employing TiCl₄ as catalyst.

The compound of formula (IV) can be prepared from the corresponding nitro compound of formula

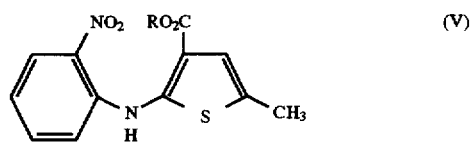

Such compounds of formula (V) in which R is an ester group, such as for example $C_{1-4}$ alkyl, are novel and form a further aspect of the invention.

If convenient this nitro compound can be converted to the amine of formula (IV) without isolation, before reaction with N-methylpiperazine. Intermediate compounds of formula (V) can be made by condensation of a thiophene of formula

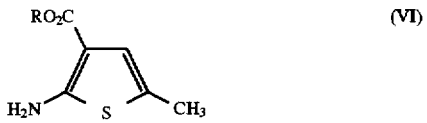

with an ortho-halonitrobenzene, preferably ortho fluoro- or chloro-nitrobenzene, in the presence of a base, for example, (a) sodium hydride in a solvent such as for example tetrahydrofuran and at a temperature of from —20° C. to 30° C., or (b) anhydrous potassium carbonate or lithium hydroxide in a solvent such as dimethylsulfoxide at a temperature of from 90° C. to 120° C. The compound of formula (V) is converted to that of formula (IV) by reduction, for example catalytically, employing hydrogen and palladium/carbon, or chemically, employing stannous chloride and hydrogen chloride in aqueous ethanol, or ammonium polysulfide, or zinc in aqueous ammonium chloride.

It will be appreciated that the compound of formula (I) may be isolated per se or may be converted to an acid addition salt using conventional methods.

The compound has an $IC_{50}$ of less than 1 mM in the $^3$H-QNB binding assay described by Yamamura, HI and Snyder, SH in Proc.Nat.Acad.Sci. USA 71 1725 (1974) indicating that it has muscarinic-cholinergic activity.

The 2-methyl-4-(4-methyl-1-piperazinyl)-10H-thieno-[2,3-b][1,5]benzodiazepine compound is effective over a wide dosage range, the actual dose administered being dependent on the condition being treated. For example, in the treatment of adult humans, dosages of from about 0.25 to 50 mg, preferably from 1 to 30 mg, and most preferably 1 to 20 mg per day may be used. A once a day dosage is normally sufficient, although divided doses may be administered. For treatment of a dyskinesia, a dose range of from 1 to 30 mg, preferably 1 to 20 mg per day is suitable. Radiolabelled 2-methyl-4-(4-methyl-1-piperazinyl)-10H-thieno-[2,3-b][1,5]benzodiazepine, can be detected in the saliva and thus the compound can potentially be monitored in patients to assess compliance.

A preferred formulation of the invention is a solid oral formulation comprising from about 1 to about 20 mg or 1 to 10 mg of active anhydrous Form I 2-methyl-4-(4-methyl-1-piperazinyl)-10H-thieno[2,3-b][1,5] benzodiazepine as an effective amount of the active ingredient.

Most preferably, the solid oral formulation is contained in packaging materials which protect the formulation from moisture and light. For example, suitable packaging materials include amber colored high density polyethylene bottles, amber colored glass bottles, and other containers made of a material which inhibits the passage of light. Most preferably, the packaging will include a desiccant pack. The container may be sealed with an aluminum foil blister to provide the desired protection and maintain product stability.

The 2-methyl-4-(4-methyl-1-piperazinyl)-10H-thieno-[2,3-b][1,5]benzodiazepine compound will normally be administered orally or by injection and, for this purpose, it is usually employed in the form of a pharmaceutical composition.

Accordingly, pharmaceutical compositions comprising 2-methyl-4-(4-methyl-1-piperazinyl)-10H-thieno[2,3-b][1,5]benzodiazepine, as active ingredient associated with a pharmaceutically acceptable carrier may be prepared. In making the compositions of the invention conventional techniques for the preparation of pharmaceutical compositions may be used. For example, the active ingredient will usually be mixed with a carrier, or diluted by a carrier, or enclosed within a carrier which may be in the form of a capsule, sachet, paper or other container. When the carrier serves as a diluent, it may be solid, semi-solid or liquid material which acts as a vehicle, excipient or medium for the active ingredient. The active ingredient can be adsorbed on a granular solid container for example in a sachet. Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxy-benzoate, talc, magnesium stearate or mineral oil. The compositions of the invention may, if desired, be formulated so as to provide quick, sustained or delayed release of the active ingredient after administration to the patient. For example, one such preferred quick release formulation is described in U.S. Pat. Nos. 5,079,018, 5,039,540, 4,305,502, 4,758,598, and 4,371,516, hereby incorporated by reference. Such formulation most preferably comprises 2-methyl-4-(4-methyl-1-piperazinyl)-10H-thieno[2,3-b][1,5] benzodiazepine, water, hydrolyzed gelatin, and mannitol.

Depending on the method of administration, the compositions for the treatment of central nervous system conditions may be formulated as tablets, capsules, injection solutions for parenteral use, gel or suspension for transdermal delivery, suspensions or elixirs for oral use or suppositories. Preferably the compositions are formulated in a unit dosage form, each dosage containing from 0.25 to 100 mg, more usually 1 to 30 mg, of the active ingredient. When a sustained release formulation is desired, the unit dosage form may contain from 0.25 to 200 mg of the active ingredient. A preferred formulation of the invention is a capsule or tablet comprising 0.25 to 75 mg or 1 to 30 mg of active ingredient together with a pharmaceutically acceptable carrier therefor. A further preferred formulation is an injection which in unit dosage form comprises 0.25 to 30 mg or 1 to 30 mg of active ingredient together with a pharmaceutically acceptable diluent therefor.

The materials for the present invention can be purchased or prepared by a variety of procedures well known to those of ordinary skill in the art. The 2-methyl-4-(4-methyl-1-piperazinyl)-10H-thieno[2,3-b][1,5] benzodiazepine compound can be prepared as described by Chakrabarti in U.S. Pat. No. 5,229,382 ('382), herein incorporated by reference in its entirety. It is most desirable to prepare a rapidly dissolving formulation comprising substantially pure crystalline Form I 2-methyl-4-(4-methyl-1-piperazinyl)-10H-thieno[2,3-b][1,5] benzodiazepine. Such substantially pure crystalline Form I 2-methyl-4-(4-methyl-1-piperazinyl)-10H-thieno[2,3-b][1,5] benzodiazepine may be prepared using the techniques described herein by the Preparation section herein infra.

As used herein mixing steps may be accomplished using common agitation methods such as stirring, shaking, and the like. As used herein the phrase "producing crystalline product from the mixture" shall refer to crystallization from the stated mixture of compound and solvent. Further, the artisan recognizes that crystallization processes may include seeding, chilling, scratching the glass of the reaction vessel, and other such common techniques.

Compound characterization methods include, for example, x-ray powder pattern analysis, thermogravimetric analysis (TGA), differential scanning calorimetery (DSC), titrametric analysis for water, and $H^1$-NMR analysis for solvent content.

The following examples are provided for purposes of illustration and are not to be construed as limiting the scope of the claimed invention.

PREPARATION 1

Crystalline Form II 2-methyl-4-(4-methyl-1-piperazinyl)-10H-thieno[2,3-b][1,5] benzodiazepine A 10 gram sample of crude 2-methyl-4-(4-methyl-1-piperazinyl)-10H-thieno[2,3-b][1,5] benzodiazepine was suspended in methylene chloride (100)gm and stirred at ambient temperature (20°–25° C.) for a period of 1 hour. The slurry was vacuum filtered and the filtrate was recovered. The stirred filtrate was chilled to 0°–5° C. in an ice bath and the solvent was slowly evaporated under a stream of nitrogen to a thick paste. Approximately ¾ of the solvent was removed by evaporation. A quantity of prechilled methylene chloride (30 gm, 0°–50° C.) was mixed into the thick paste. The resulting slurry was vacuum filtered and allowed to air dry on the filter. The isolated solid was further dried in a vacuum oven at 50° C. for a period of 30 minutes. Isolated: 4.8 gm. X-ray powder characterization: Form II+CH$_2$Cl$_2$ Solvate.

The isolated solid was redried in a vacuum oven at 50° C. under a stream of nitrogen for a period of 30 hours. Isolated: 4.5 gm X-ray powder characterization: Form II. (described supra.)

PREPARATION 2

Form I 2-methyl-4-(4-methyl-1-piperazinyl)-10H-thieno[2,3-b][1,5] benzodiazepine A sample of ethyl acetate which was saturated with technical grade 2-methyl-4-(4-methyl-1-piperazinyl)-10 H-thieno[2,3-b][1,5] benzodiazepine was contacted with Form II 2-methyl-4-(4-methyl-1-piperazinyl)-10H-thieno[2,3-b][1,5] benzodiazepine (0.3g), a seed of anhydrous Form I 2-methyl-4-(4-methyl-1-piperazinyl)-10H-thieno[2,3-b][1,5] benzodiazepine and stirred at about 25° C. for about 5 hours. The reaction product was isolated by vacuum filtration and dried under ambient conditions. Yield: 0.25 g. X-ray powder analysis indicated that the product was anhydrous Form I 2-methyl-4-(4-methyl-1-piperazinyl)-10H-thieno[2,3-b][1,5] benzodiazepine.

PREPARATION 3

Technical Grade 2-methyl-4-(4-methyl-1-piperazinyl)-10H-thieno[2,3-b][1,5] benzodiazepine

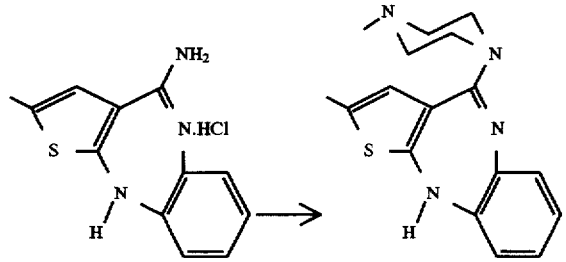

Intermediate 1

In a suitable three neck flask the following was added:

Dimethylsulfoxide (analytical): 6 volumes

Intermediate 1: 75 g

N-Methylpiperazine (reagent): 6 equivalents

Intermediate 1 can be prepared using methods known to the skilled artisan. For example, the preparation of the Intermediate 1 is taught in the '382 patent.

A sub-surface nitrogen sparge line was added to remove the ammonia formed during the reaction. The reaction was heated to 120° C. and maintained throughout the duration of the reaction. The reactions were followed by HPLC until ≦5% of the intermediate 1 was left unreacted. After the reaction was complete, the mixture was allowed to cool slowly to 20° C. (about 2 hours). Each reaction mixture was then transferred to an appropriate three neck round bottom flask and water bath. To this solution with agitation was added 10 volumes reagent grade methanol and the reaction was stirred at 20° C. for 30 minutes. Three volumes of water was added slowly over about 30 minutes. The reaction slurry was cooled to zero to 5° C. and stirred for 30 minutes. The product was filtered and the wet cake was washed with chilled methanol. The wet cake was dried in vacuo at 45° C. overnight. The product was identified as technical 2-methyl-4-(4-methyl-1-piperazinyl)-10H-thieno[2,3-b] [1,5] benzodiazepine.

Yield: 76.7%; Potency: 98.1%

The procedure of Preparation 3 was repeated substantially as described above and provided a yield of 81% with a potency of 101.1%.

PREPARATION 4

Technical Grade 2-methyl-4-(4-methyl-1-piperazinyl)-10H-thieno[2,3-b] [1,5] benzodiazepine Intermediate 1 (supra) was suspended in DMSO (3.2 vol.) and toluene (4.5 vol.). A portion (≈0.65 vol.) of the solvent was removed by distillation at 120°–125° C. The mixture was cooled to 110° C.. N-methylpiperazine(NMP, 4.2 equiv.) was added and the mixture heated back to reflux (120°–125° C). Another portion (≈1 vol.) of the solvent was removed by distillation to dry the reaction mixture. A vigorous reflux was desired to drive the reaction to completion (about 7 hrs.) by removing ammonia from the reaction. The product was isolated by the slow addition of water (12.75 vol.) to the cooled (10° C.) reaction solution. The product was collected by filtration and washed with chilled water (2 vol.). The crude 2-methyl-4-(4-methyl-1-piperazinyl)-10H-thieno[2,3-b][1,5] benzodiazepine was dried in vacuo at 60° C. The product was recrystallized from hot toluene (5 vol.) to give a technical grade 2-methyl-4-(4-methyl-1-piperazinyl)-10H-thieno[2,3-b][1,5] benzodiazepine. After drying in vacuo at 50° C.. the technical grade 2-methyl-4-(4-methyl-1-piperazinyl)-10H-thieno[2,3-b] [1,5] benzodiazepine was recrystallized again from ethyl acetate (10 vol.)/toluene (0.62 vol.)/methanol (3.1 vol.)to give 2-methyl-4-(4-methyl-1-piperazinyl)-10H-thieno[2,3-b] [1,5] benzodiazepine as a methanol solvate. The methanol solvate upon drying at >50° C. was converted to an anhydrous technical grade 2-methyl-4-(4-methyl-1-piperazinyl)-10H-thieno[2,3-b][1,5] benzodiazepine.

PREPARATION 5

Form I from Acetone

A 3.0 g sample of technical grade 2-methyl-4-(4-methyl-1-piperazinyl)-10H-thieno[2,3-b][1,5] benzodiazepine was suspended in acetone (30 g). The mixture was stirred and heated to about 60° C. The mixture was maintained at about 60° C. for about 30 minutes. The mixture was allowed to cool to about 25° C. The resulting product was isolated using vacuum filtration. The product was identified as Form I 2-methyl-4-(4-methyl-1-piperazinyl)-10H-thieno[2,3-b] [1,5] benzodiazepine using x-ray powder analysis. Yield: 0.8 g.

PREPARATION 6

Form I Using Tetrahydrofuran

An 8.0 g sample of technical grade 2-methyl-4-(4-methyl-1-piperazinyl)-10H-thieno[2,3-b][1,5] benzodiazepine was suspended in tetrahydrofuran (25 g). The mixture was stirred and heated to about 60° C. The mixture was maintained at about 60° C. for about 30 minutes. The mixture was allowed to cool to about 25° C. The resulting product was isolated using vacuum filtration. The product was identified as Form I 2-methyl-4-(4-methyl-1-piperazinyl)-10H-thieno[2,3-b][1,5] benzodiazepine using x-ray powder analysis. Yield: 1.3 g.

PREPARATION 7

Form I Using Ethyl Acetate

A 270 g sample of technical grade 2-methyl-4-(4-methyl-1-piperazinyl)-10H-thieno[2,3-b][1,5] benzodiazepine was suspended in ethyl acetate (2.7 L). The mixture was heated to about 76° C. and maintained at about 76° C. for about 30 minutes. The mixture was allowed to cool to about 25° C. The resulting product was isolated using vacuum filtration. The product was identified as Form I 2-methyl-4-(4-methyl-1-piperazinyl)-10H-thieno[2,3-b][1,5] benzodiazepine using x-ray powder analysis.

Yield: 197 g.

PREPARATION 8

Form I from t-butanol

A 1.0 g sample of technical grade 2-methyl-4-(4-methyl-1-piperazinyl)-10H-thieno[2,3-b][1,5] benzodiazepine was suspended in tert-butanol (30 g). The stirred mixture was heated to about 60° C. and maintained at about 60° C. for about 30 minutes. The mixture was allowed to cool to about 25° C. The resulting product was isolated using vacuum filtration. The product was identified as Form I 2-methyl-4-(4-methyl-1-piperazinyl)-10H-thieno[2,3-b][1,5] benzodiazepine using x-ray powder analysis.

Yield: 0.3 g.

PREPARATION 9

Form I from Slurry Conversion of Form II in Toluene

A 0.5 g sample of technical grade 2-methyl-4-(4-methyl-1-piperazinyl)-10H-thieno[2,3-b][1,5]benzodiazepine and a 0.5 g sample of Form II 2-methyl-4-(4-methyl-1-piperazinyl)-10H-thieno[2,3-b][1,5]benzodiazepine were suspended in toluene (5 ml), presaturated with 2-methyl-4-(4-methyl-1-piperazinyl)-10H-thieno[2,3-b][1,5] benzodiazepine. The mixture was stirred in a sealed vial at about ambient temperature for about 22 hours. The resulting product was isolated using vacuum filtration and dried under vacuum at about 45° C. The product was identified as Form I 2-methyl-4-(4-methyl-1-piperazinyl)-10H-thieno[2,3-b][1,5]benzodiazepine using x-ray powder analysis.

EXAMPLE 1

A portion of the hydroxypropyl cellulose was dissolved in purified water to form a solution for granulation. The remaining hydroxypropyl cellulose (total of 4.0% w/w final tablet weight), which was an extra fine grade, was combined with the 2-methyl-4-(4-methyl-1-piperazinyl)-10H-thieno [2,3-b][1,5] benzodiazepine (1.18% w/w), lactose (79.32% w/w) and a portion of the crospovidone (5% w/w) in a high shear granulator. All ingredients were security sieved prior to addition and dry blended in the granulator. This mixture was then granulated with the hydroxypropyl cellulose solution in the high shear granulator. The granulation was wet sized using standard methods. The wet granulation was then dried in a fluidized bed dryer and sized. The material was then added to a tumble bin mixer.

The running powders consisting of microcrystalline cellulose (granular) (10% w/w), magnesium stearate (0.5% w/w), and the remainder of the crospovidone were added to the sized granulation. The mixture was blended and compressed with the appropriate tooling on tablet compression equipment.

Subcoating

Hydroxypropyl methylcellulose (10% w/w) was mixed with purified water to form a solution. Core tablets were divided into approximately equal sections and spray coated with the hydroxypropyl methylcellulose solution. The operation was performed in a perforated coating pan.

Coating of Core Tablets

Color Mixture White (hydroxypropyl methylcellulose, polyethylene glycol, polysorbate 80, and titanium dioxide) was mixed with purified water to form the coating suspension.

Subcoated tablets were divided into approximately equal sections and spray coated with the coating suspension described above. The operation was performed in a perforated coating pan.

The coated tablets were lightly dusted with carnauba wax and imprinted with appropriate identification.

EXAMPLE 2

The process substantially as described above in Example 1 was repeated using the following ingredients to provide pharmaceutically elegant tablet formulations containing 1, 2.5, 5, 7.5, and 10 mg 2-methyl-4-(4-methyl-1-piperazinyl)-10H-thieno[2,3-b][1,5] benzodiazepine, respectively, per tablet:

1 mg 2-methyl-4-(4-methyl-1-piperazinyl)-10H-thieno[2,3-b][1,5] benzodiazepine per tablet

| Names of Ingredients | Quantity (mg/tablet) |
| --- | --- |
| Active Ingredient | |
| 2-methyl-4-(4-methyl-1-piperazinyl)-10H-thieno[2,3-b] [1,5] benzodiazepine | 1.0 |
| Other Ingredients | |
| Lactose | 67.43 |
| Hydroxypropyl Cellulose | 3.40 |
| Crospovidone | 4.25 |
| Microcrystalline Cellulose | 8.50 |

-continued

| Names of Ingredients | Quantity (mg/tablet) |
|---|---|
| Magnesium Stearate Subcoating | 0.42 |
| Hydroxypropyl Methylcellulose Coating | 1.70 |
| Color Mixture White Polishing | 3.47 |
| Carnauba Wax Imprinting | trace |
| Edible Blue Ink | trace |

2-methyl-4-(4-methyl-1-piperazinyl)-10H-thieno[2,3-b][1,5] benzodiazepine 2.5 mg Tablets

| Names of Ingredients | Quantity (mg/tablet) |
|---|---|
| Active Ingredient | |
| 2-methyl-4-(4-methyl-1-piperazinyl)-10H-thieno[2,3-b][1,5]benzodiazepine | 2.5 |
| Other Ingredients | |
| Lactose | 102.15 |
| Hydroxypropyl Cellulose | 5.20 |
| Crospovidone | 6.50 |
| Microcrystalline Cellulose | 13.00 |
| Magnesium Stearate Subcoating | 0.65 |
| Hydroxypropyl Methylcellulose Coating | 2.60 |
| Color Mixture White Polishing | 5.30 |
| Carnauba Wax Imprinting | trace |
| Edible Blue Ink | trace |

2-methyl-4-(4-methyl-1-piperazinyl)-10H-thieno[2,3-b][1,5] benzodiazepine 5.0 mg Tablets

| Names of Ingredients | Quantity (mg/tablet) |
|---|---|
| Active Ingredient | |
| 2-methyl-4-(4-methyl-1-piperazinyl)-10H-thieno[2,3-b][1,5]benzodiazepine | 5.00 |
| Other Ingredients | |
| Lactose | 156.00 |
| Hydroxypropyl Cellulose | 8.00 |
| Crospovidone | 10.00 |
| Microcrystalline | 20.00 |

-continued

| Names of Ingredients | Quantity (mg/tablet) |
|---|---|
| Cellulose | |
| Magnesium Stearate Subcoating | 1.00 |
| Hydroxypropyl Methylcellulose Coating | 4.00 |
| Color Mixture White Polishing | 8.16 |
| Carnauba Wax Imprinting | trace |
| Edible Blue Ink | trace |

2-methyl-4-(4-methyl-1-piperazinyl)-10H-thieno[2,3-b][1,5] benzodiazepine 7.5 mg Tablets

| Names of Ingredients | Quantity (mg/tablet) |
|---|---|
| Active Ingredient | |
| 2-methyl-4-(4-methyl-1-piperazinyl)-10H-thieno[2,3-b][1,5]benzodiazepine | 7.50 |
| Other Ingredients | |
| Lactose | 234.00 |
| Hydroxypropyl Cellulose | 12.00 |
| Crospovidone | 15.00 |
| Microcrystalline Cellulose | 30.00 |
| Magnesium Stearate Subcoating | 1.50 |
| Hydroxypropyl Methylcellulose Coating | 6.00 |
| Color Mixture White Polishing | 12.24 |
| Carnauba Wax Imprinting | trace |
| Edible Blue Ink | trace |

2-methyl-4-(4-methyl-1-piperazinyl)-10H-thieno[2,3-b][1,5] benzodiazepine 10.0 mg Tablets

| Names of Ingredients | Quantity (mg/tablet) |
|---|---|
| Active Ingredient | |
| 2-methyl-4-(4-methyl-1-piperazinyl)-10H-thieno[2,3-b][1,5]benzodiazepine | 10.00 |
| Other Ingredients | |
| Lactose | 312.00 |
| Hydroxypropyl Cellulose | 16.00 |
| Crospovidone | 20.00 |

-continued

| Names of Ingredients | Quantity (mg/tablet) |
|---|---|
| Microcrystalline Cellulose | 40.00 |
| Magnesium Stearate Subcoating | 2.00 |
| Hydroxypropyl Methylcellulose Coating | 8.00 |
| Color Mixture White Polishing | 16.32 |
| Carnauba Wax Imprinting | trace |
| Edible Blue Ink | trace |

EXAMPLE 4

Pulvule Formulation

A pulvule formulation is prepared by blending the active with silicone starch, and filling it into hard gelatin capsules.

|  | Per 300 mg capsule |
|---|---|
| Compound of the invention | 30.0 mg |
| Silicone | 2.9 mg |
| Starch flowable | 267.1 mg |

EXAMPLE 5

Tablet Formulation

A tablet formulation is made by granulating the active with appropriate diluent, lubricant, disintegrant and binder and compressing

| Compound of the invention | 10.0 mg |
|---|---|
| Magnesium stearate | 0.9 mg |
| Microcrystalline cellulose | 75.0 mg |
| Povidone | 15.0 mg |
| Starch, directly compressible | 204.1 mg |

EXAMPLE 6

Aqueous Injection Formulation

An aqueous injection of active is prepared as a freeze-dried plug, for reconstitution in a suitable, sterile diluent before use (to a total volume of 10 ml).

Compound of the invention is contacted with Mannitol N Hydrochloric acid and/or N sodium hydroxide to adjust pH to 5–5.5.

| Compound of the invention | 20.0 mg |
|---|---|
| Mannitol | 20.0 mg |
| N Hydrochloric acid and/or N sodium hydroxide to adjust pH to 5–5.5. | |

EXAMPLE 7

Controlled Release IM Formulation

A controlled release injection for intramuscular injection is formed from a sterile suspension of micronised active in an oleaginous vehicle.

| Compound of the invention | 50.0 mg |
|---|---|
| Aluminium stearate | 0.04 mg |
| Sesame oil | 2 ml |

EXAMPLE 8

Capsule Formulation

A formulation is prepared by blending the active with silicone starch and starch, and filling it into hard gelatine capsules.

|  | Per 300 mg capsule |
|---|---|
| Compound of the invention | 2.5 mg |
| Starch flowable with 0.96% silicone 220 | 222.5 mg |
| Starch flowable | 75.0 mg |

EXAMPLE 9

2-methyl-4-(4-methyl-1-piperazinyl)-10H-thieno[2,3-b][1,5] benzodiazepine Granules The granules were produced by blending the mannitol and Hydroxymethyl propyl cellulose in a high shear mixer; granulating with the aqueous suspension of 2-methyl-4-(4-methyl-1-piperazinyl)-10H-thieno[2,3-b][1,5] benzodiazepine and polysorbate 20; wet sized and subsequently dried in a fluid bed dryer. These are dry sized and reblended prior to packaging.

| INGREDIENT | MG/SACHET |
|---|---|
| 1a. 250 mg Sachets | |
| Active | |
| 2-methyl-4-(4-methyl-1-piperazinyl)-10H-thieno[2,3-b] [1,5] benzodiazepine | 2.50 |
| Other Ingredients | |
| Mannitol | 234.97 |
| Hydroxypropyl methyl cellulose 3 cps | 12.50 |
| Polysorbate 20 | 0.028 |
| 1b. 750 mg Sachets | |
| Active | |
| 2-methyl-4-(4-methyl-1-piperazinyl)-10H-thieno[2,3-b] [1,5] benzodiazepine | 7.50 |
| Other Ingredients | |
| Mannitol | 704.93 |
| Hydroxypropyl methyl cellulose 3 cps | 37.49 |
| Polysorbate 20 | 0.08 |

-continued

| INGREDIENT | MG/SACHET |
|---|---|
| 1c. 1000 mg Sachets | |
| Active | |
| 2-methyl-4-(4-methyl-1-piperazinyl)-10H-thieno[2,3-b][1,5]benzodiazepine | 10.0 |
| Other Ingredients | |
| Mannitol | 939.90 |
| Hydroxypropyl methyl cellulose 3 cps | 49.99 |
| Polysorbate 20 | 0.11 |

Such granules are most preferably contacted with an acidic medium if a suspension or solution is desired.

I claim:

1. A method for treating a dopaminergic-mediated dyskinesia selected from drug-induced dyskinesia, athetosis, chorea, choreoathetosis, tardive dyskinesia and tardive dystonia comprising administering to a mammal in need of such treatment, an effective amount of olanzapine, or a pharmaceutically acceptable salt thereof.

2. A method of claim 1 wherein the olanzapine is substantially pure Form I olanzapine.

3. A method of claim 1 wherein the dyskinesia is a hyperkinesia.

4. A method of claim 2 wherein the dyskinesia is tardive dyskinesia.

5. A method of claim 1 wherein the effective amount is from about 1 mg to about 20 mg per day.

6. A method of claim 1 wherein the dyskinesia is a chorea.

7. A method of claim 1 wherein the dyskinesia is an athetosis.

8. A method of claim 1 wherein the dyskinesia is drug-induced.

9. A method of claim 1 wherein the dyskinesia is naturally occurring.

10. A method of claim 1 wherein the dyskinesia is choreathetosis.

11. A method of claim 1 wherein the dyskinesia is selected from the group consisting of tardive dystonia and tardive dyskinesia.

* * * * *